United States Patent [19]

Karamian

[11] 4,093,381
[45] June 6, 1978

[54] METHOD FOR ASSAYING ENDOTOXINS

[76] Inventor: Narbik A. Karamian, 7609 Exeter Rd., Bethesda, Md. 20014

[21] Appl. No.: 745,966

[22] Filed: Nov. 29, 1976

[51] Int. Cl.² ............................................. G01N 21/00
[52] U.S. Cl. .............................. 356/51; 195/103.5 R; 23/230 B; 250/373
[58] Field of Search .................. 195/103.5 R; 356/51, 356/201; 23/230 B; 250/373

[56] References Cited

U.S. PATENT DOCUMENTS

| 3,327,119 | 6/1967 | Kamentsky | 356/51 |
| 3,944,391 | 3/1976 | Harris et al. | 195/103.5 R |

Primary Examiner—Alvin E. Tanenholtz
Attorney, Agent, or Firm—Joseph P. Nigon

[57] ABSTRACT

A new convenient and more reliable spectrophotometric method for assaying endotoxins at levels as low as 10 ppb. Five different solutions of endotoxins, *E. coli* 0127:B8, *E. coli* 055:B5, *S. abortus equi*, *S. enteritidis* and *S. flexneri* were examined and each exhibited an absorption maximum of 259 mm.

3 Claims, No Drawings

METHOD FOR ASSAYING ENDOTOXINS

BACKGROUND OF THE INVENTION

Endotoxins, which are commonly known as pyrogens, are substances produced by microorganisms growing in water or in aqueous solutions. They cause inflammation and general fever when injected intravenously. They are colloidal in nature and they persist even after the organisms which produce them are destroyed by sterilization.

Neither the mode(s) of their activity nor their structures are known. However, in general, it is known that in gram-negative bacteria, the glycopeptide basal layer is covered with a lipopolysaccharide which constitutes 20-30% of the cell wall. Lipopolysaccharides, components of the whole somatic antigen, with molecular weights of the order of $10^6$ to $10^7$, exhibit endotoxin activity. It is difficult to construct a molecular model for a lipopolysaccharide which would adequately explain the shapes revealed by electron microscopy.

Endotoxins of high antigentic activity have been extracted from bacteria by using one of the recognized published procedures. The best known are the Boivin trichloroacetic acid procedure (Boivin, A., and Mesrobeanie, L., Compt. Rend. Soc. Biol. 113,490, (1933); 128,5 (1938): as modified by Webster, Sagin, Landy and Johnson (Webster, M. E., Sagin, J. F., Landy, M. and Johnson, A., J. Immunology, 74,455 (1955), and the trypsin digestion method of Hartwell and Shear (Hartwell, J. L., and Shear, M. J. J Nat. Cancer Inst., 4, 107–22, (1943). These methods produce bacterial endotoxins possessing properties adequate for most immunological and pathological studies. The purified endotoxins are comparatively stable in the solid form, but they may become inactivated in solution by hydrolysis.

Shigella dysenteriae has been proposed as an international reference bacterium for preparing endotoxins for pyrogenic activity. The endotoxin derived from this source contains 4.504.6% nitrogen and 0.80–085% phosphorus. It has a molecular weight of about $10^7$ and a strong pyrogenic activity at a level of 0.01 ppm in water (Humphrey, J. H., and Bangham, D. R., Bull Org. Mond. Sante, 20, 1231–44 (1959).

The first significant pyrogenic work was done between 1911–1916 by Jona (Jona, J. L., Med. J. of Australia iii, 71–73 (1916) and Hort and Penfield (Hort, E. C., and Penfield, W. J., Britt. Med. J., 2, 1589 (1911). They discovered that intravenous infusions cause elevation of body temperature. In their work freshly prepared distilled water was injected into both a man and animals as a control. A portion of the same distilled water was innoculated into an unsterile container for a period of time and this preparation was then injected into the same man and animals. The febrile reaction occurred only when the innoculated distilled water was injected into the unsterile container. They concluded that the fever-causing product, called pyrogen, was associated with bacteria but was not a part of the bacteria themselves since autoclaving, boiling and filtering did not reverse the febrile reaction. They also were able to classify microorganisms into pyrogenic-type gram negative and nonpyrogenic-type gram positive. Because of the lack of advanced equipment and knowledge their experiments were limited, but they formed the basis for the development of the modern standardized pyrogen test. Siebert (Siebert, F. B., Amer, J. Physiol. 67, 90–04 (1923), (Siebert, F. B., Amer. J. Physiol., 71, 621-51 (1925), in 1923, confirmed these observations by injecting distilled water into rabbits. In her experiments she demonstrated that bacterial products are present in all pyrogenic fluids that are unaffected by autoclaving, boiling and filtering techniques. She concluded that pyrogenic reactions occur even in sterile fluids and that pyrogenic reactions reactions can be prevented in pharmaceutical preparations only by the removal of pyrogens.

In the conventional method parenteral solutions are examined for pyrogens by using rabbits as test animals according to the procedure outlined in the United States Pharmacopeia (USP) This procedure was adopted in the early 1940's when the need for an official pyrogen test was first recognized. A collaborative study was undertaken by the Food and Drug Administration, the National Institutes of Health, and 14 pharmaceutical manufacturing companies. As a result of these studies, the first official pyrogen test was adopted and appeared in the XIIth Revision of the United States Pharmacopeia. Pharmaceutical companies and research laboratories have made extensive use of the USP rabbit pyrogen test during the past 35 years because of its low cost and the ease with which the rabbits are handled during the test. However, other animals such as dogs, cats, monkeys, and horses are equally reliable for the test. The rabbit is reported to be the most sensitive animal for indicating the absence of pyrogens, whereas the dog is the most sensitive animal for establishing the presence of pyrogens. Some investigators have used both animals in order to obtain a better indication, particularly in doubtful cases.

The test is performed in a room in which the temperature and humidity are maintained at the same levels as the room in which the animals are housed.

The USP test requires the use of healthy mature rabbits of either sex weighing not less than 1500 grams. However, to avoid the emotional stimuli which occur when males and females are mixed, most laboratories use rabbits of a single sex. Animals eliciting a negative pyrogen reaction may be used again after 48 hours and those eliciting a positive pyrogen reaction may be used after a two-week rest period.

The test animals are fed until an hour before the first temperature reading is made and they are not fed, with the exception of water, until the one-day test period is over. On the day of the test, the initial temperatures of the animals are recorded. Rabbits with initial control temperatures above 39.8° C are rejected for the test.

All syringes, needles and glassware used for the injections are prepared in advance by heating at 250° C in a muffle furnace for at least 30 minutes. This process renders the implements pyrogen-free and they can then be sterilized.

Since rectal temperature probes, clinical thermometers and electric or digital recording devices must remain in place throughout the pyrogen test, the animals must be restrained. This is usually accomplished with restraining boxes.

Prior to injection, samples are made isotonic with pyrogen-free sodium chloride and warmed to 37° C. Then 10 ml of the sample per kilogram of body weight of the animal are injected into each of 3 selected rabbits through the ear vein. Then, the maximum temperature-rise over a period of several hours is noted for each rabbit. A negative test is indicated when no rabbit shows an individual rise in temperature of 0.6° C or more above its respective control temperature, of if the sum of the 3-rabbit temperature rises does not exceed 1.4° C. The test is repeated with 5 rabbits. If 3 or less of the total of 8 rabbits show individual temperature rises of 0.6° C or more, and if the sum of the temperature rises for all rabbits does not exceed 3.7° C, the sample is nonpyrogenic.

A test with a slight variations from the USP test is formulated in the United States Public Health Service (PHS) Regulations for the official pyrogen test for biologic products. At the final point, these regulations state that a negative pyrogen test of a product is indicated when less than one-half of the 3 or more test rabbits show individual temperature rises of 0.6° C or less, or if the average temperature rise of all test rabbits is less than 0.5° C.

In 1971, Reinhold and Fine (Reinhold, R. B. Fine, J., Proc. Soc. Exp. Biol. Med. 137, 334–40 (1971), developed a specific in vitro assay method, the 'Limulus Amebocyte Lysate Test', which has a sensitivity level of 0.001–0.005 mg of pyrogen per ml of human plasma. The test is performed by mixing the sample with a cell lysate which is extracted from the circulating amebocytes of *Limulus polyphemus* (horseshoe crab). If sufficient pyrogen is present in the sample, the lysate will gel; otherwise, the bulk of the solution will remain fluid indicating a negative test.

Although the test will normally detect a low level of endotoxins, it has not been used widely with sufficient confidence to replace the present rabbit test, primarily because there is a borderline region in the gelatin process wherein the analyst must rely heavily on his visual judgment. Also, the gel-forming reaction is quite delicate and it is irreversibly terminated with improper care.

BRIEF DESCRIPTION OF THE INVENTION

An analytical method has been developed which is capable of detecting pyrogens at the 10 parts per billion (ppb) level. The method depends on the measurement of the ultra-violet spectrum of solutions containing the pyrogens over the 200 to 800 nm range using the equipment described below. The absorption at 259 nm measures the concentration of endotoxins.

DETAILED DESCRIPTION OF THE INVENTION

An absorption spectrum is obtained by placing a substance in a suitable cell and exposing it to the energy source of interest in the frequency range being studied. The spectrophotometer is designed so that it measures the transmitted energy relative to the incident energy at a given frequency. The energy required to excite an electron in a compound from its ground state molecular orbital to an excited state is directly proportional to the frequency of the radiation that causes the transition:

$$E_2 - E_1 = h\nu$$

where $E_2$ and $E_1$ are the energies of the initial and final states, respectively, $h$ is Planck's constant, $6.624 \times 10^{-27}$ erg-sec and $\nu$ is the frequency of the incident radiation.

When a molecule absorbs electromagnetic radiation in the ultra-violet or visible region, the electronic transitions are accompanied by the lower-energy vibronic and rotational transitions of the molecule as a whole as well as those of the individual chemical bonds within the molecule. These cause absorption bands to appear in the spectrum.

Such absorption is described by the Beer-Lambert law. Beer's law states that in a non-absorbing solvent, each solute molecule absorbs the same fraction of incident light regardless of the concentration. This law is valid only in dilute solutions. Lambert's law states that the intensity of light passing through a homogeneous medium decreases logarithmically as the thickness of the layer increases. The combined laws may be written:

$$A = \log(io/I) = \epsilon l c$$

where:
 $A$ is the absorbance.
 $Io$ is the intensity of incident light.
 $I$ is the intensity of transmitted light.
 $l$ is the cell thickness in cm.
 $c$ is the concentration in mole/liter.
 $\epsilon$ is the molar absorptivity or extinction coefficient in liters/mole-cm.

Modern ultra-violet/visible spectrophotometers can commonly measure spectra from 180 nm to 800 nm.

My invention is illustrated by the following specific but non-limiting example.

EXAMPLE

An ACTA MVI Spectrophotometer was used for measuring the absrobance of endotoxin solutions over a concentration range of 10 to 10,000 ppb.

Endotoxins

Lipopolysaccharide *E. coli* 0127:B8
Lipopolysaccharide *E. coli* 055:B5
Lipopolysaccharide *S. abortus equi*
Lipopolysaccharide *S. enteritidis*
Lipopolysaccharide *S. flexneri*

All endotoxins were prepared commercially by the Westphal extraction method and were shipped in powder form in vials that must be kept refrigerated.

Since the endotoxins have low solubilities in water, all stock solutions were prepared at 50 ppm concentrations. The solutions were prepared by dissolving 50 mg of each endotoxin in 1-liter of endotoxin-free distilled water.

Before measuring the endotoxin concentrations it was necessary to establish the wavelength of maximum absorption. It was also necessary to establish that the endotoxin absorption followed Beer's law.

The stock solutions were diluted to 7.5 ppm with endotoxin-free distilled water and the absorption curve of each was run in a 10-cm cell in order to establish its wavelength of maximum absorption. The data for *E. coli* 1027:B8, *E. coli* 055:B5, *S. abortus equi*, *S. enteritidis* and *S. flexneri* are presented in Tables 1 through 5. A solution containing a mixture of five endotoxins was prepared. It consisted of 50 ppm of each of the endotoxins cited above. This stock solution was diluted, as above, to 7.5 ppm and its absorption curve was run. The data are presented in Table 6.

TABLE 1
UV ABSORPTION DATA FOR BACTO-LIPOPOLYSACCHARIDE *E. COLI* 0127:B8

| Wavelength nm | Slit Width mm | Absorbance | Transmittance Per Cent |
|---|---|---|---|
| 200 | 2.00 | 1.150 | 7.5 |
| 220 | 0.28 | 0.473 | 33.8 |
| 225 | 0.24 | 0.342 | 45.5 |
| 230 | 0.22 | 0.297 | 50.5 |

TABLE 1-continued
UV ABSORPTION DATA FOR BACTO-LIPOPOLYSACCHARIDE E. COLI 0127:B8

| Wavelength nm | Slit Width mm | Absorbance | Transmittance Per Cent |
|---|---|---|---|
| 233 | 0.20 | 0.300 | 50.0 |
| 234 | 0.20 | 0.304 | 49.6 |
| 235 | 0.20 | 0.314 | 48.8 |
| 240 | 0.19 | 0.372 | 42.3 |
| 245 | 0.18 | 0.458 | 35.0 |
| 250 | 0.17 | 0.544 | 28.6 |
| 255 | 0.16 | 0.598 | 25.2 |
| 259 | 0.16 | 0.606 | 24.8 |
| 260 | 0.16 | 0.605 | 24.9 |
| 263 | 0.16 | 0.582 | 26.2 |
| 265 | 0.16 | 0.560 | 27.7 |
| 270 | 0.16 | 0.487 | 32.8 |
| 275 | 0.16 | 0.402 | 39.8 |
| 280 | 0.15 | 0.316 | 48.2 |
| 285 | 0.15 | 0.233 | 58.5 |
| 290 | 0.15 | 0.162 | 69.0 |
| 295 | 0.14 | 0.102 | 79.2 |

4.5 ml of 50 ppm E. Coli 0127:B8 were diluted to 30 ml. The final concentration is 7.5 ppm.

TABLE 2
UV ABSORPTION DATA FOR BACTO-LIPOPOLYSACCHARIDE E. COLI 055:B5

| Wavelength nm | Silt Width mm | Absorbance | Transmittance Per Cent |
|---|---|---|---|
| 220 | 0.28 | 0.300 | 50.0 |
| 225 | 0.24 | 0.217 | 60.6 |
| 230 | 0.22 | 0.177 | 66.8 |
| 233 | 0.20 | 0.172 | 67.2 |
| 234 | 0.20 | 0.174 | 67.0 |
| 235 | 0.20 | 0.175 | 67.0 |
| 240 | 0.19 | 0.191 | 64.4 |
| 245 | 0.18 | 0.225 | 60.2 |
| 250 | 0.17 | 0.255 | 55.5 |
| 255 | 0.16 | 0.275 | 53.0 |
| 259 | 0.16 | 0.280 | 52.5 |
| 260 | 0.16 | 0.280 | 52.5 |
| 263 | 0.16 | 0.275 | 53.0 |
| 265 | 0.16 | 0.270 | 54.3 |
| 270 | 0.16 | 0.240 | 57.5 |
| 275 | 0.16 | 0.202 | 63.0 |
| 280 | 0.15 | 0.162 | 68.9 |
| 285 | 0.15 | 0.125 | 75.0 |
| 290 | 0.15 | 0.095 | 80.2 |
| 295 | 0.14 | 0.069 | 85.1 |

4.5 ml of 50 ppm E. coli 055:B5 were diluted to 30 ml. The final solution concentration is 7.5 ppm.

TABLE 3
UV ABSORPTION DATA FOR BACTO-LIPOPOLYSACCHARIDE S. ABORTUS EQUI

| Wavelength nm | Slit Width mm | Absorbance | Transmittance Per Cent |
|---|---|---|---|
| 220 | 0.28 | 0.343 | 45.3 |
| 225 | 0.24 | 0.250 | 56.2 |
| 230 | 0.22 | 0.210 | 61.5 |
| 233 | 0.20 | 0.209 | 61.8 |
| 234 | 0.20 | 0.212 | 61.1 |
| 235 | 0.20 | 0.217 | 60.8 |
| 240 | 0.19 | 0.260 | 55.0 |
| 245 | 0.18 | 0.325 | 47.2 |
| 250 | 0.17 | 0.390 | 40.8 |
| 255 | 0.16 | 0.425 | 37.5 |
| 259 | 0.16 | 0.435 | 36.8 |
| 260 | 0.16 | 0.434 | 36.7 |
| 263 | 0.16 | 0.421 | 38.0 |
| 265 | 0.16 | 0.410 | 39.0 |
| 270 | 0.16 | 0.365 | 43.0 |
| 275 | 0.16 | 0.310 | 49.0 |
| 280 | 0.15 | 0.255 | 55.6 |
| 285 | 0.15 | 0.195 | 63.8 |
| 290 | 0.15 | 0.145 | 72.0 |
| 295 | 0.14 | 0.095 | 80.2 |

4.5 ml of 50 ppm S. abortus equi were diluted to 30 ml. The final concentration is 7.5 ppm.

TABLE 4
UV ABSORPTION DATA FOR BACTO-LIPOPOLYSACCHARIDE S. ENTERITIDIS

| Wavelength nm | Slit Width mm | Absorbance | Transmittance Per Cent |
|---|---|---|---|
| 220 | 0.28 | 0.355 | 44.0 |
| 225 | 0.24 | 0.264 | 54.6 |
| 230 | 0.22 | 0.225 | 59.7 |
| 233 | 0.20 | 0.224 | 59.8 |
| 234 | 0.20 | 0.228 | 59.1 |
| 235 | 0.20 | 0.232 | 58.8 |
| 240 | 0.19 | 0.273 | 53.2 |
| 245 | 0.18 | 0.332 | 46.5 |
| 250 | 0.17 | 0.395 | 40.1 |
| 255 | 0.16 | 0.430 | 37.0 |
| 259 | 0.16 | 0.437 | 36.7 |
| 260 | 0.16 | 0.434 | 36.8 |
| 263 | 0.16 | 0.420 | 38.0 |
| 265 | 0.16 | 0.405 | 39.5 |
| 270 | 0.16 | 0.360 | 43.5 |
| 275 | 0.16 | 0.305 | 49.8 |
| 280 | 0.15 | 0.245 | 57.0 |
| 285 | 0.15 | 0.185 | 65.5 |
| 290 | 0.15 | 0.135 | 73.4 |
| 295 | 0.14 | 0.092 | 81.0 |

4.5 ml of 50 ppm S. enteritidis were diluted to 30 ml. The final concentration is 7.5 ppm.

TABLE 5
UV ABSORPTION DATA FOR BACTO-LIPOPOLYSACCHARIDE S. FLEXNERI

| Wavelength nm | Slit Width mm | Absorbance | Transmittance Per Cent |
|---|---|---|---|
| 220 | 0.28 | 0.410 | 39.0 |
| 225 | 0.24 | 0.310 | 49.0 |
| 230 | 0.22 | 0.260 | 55.0 |
| 233 | 0.20 | 0.255 | 55.6 |
| 234 | 0.20 | 0.257 | 55.2 |
| 235 | 0.20 | 0.260 | 55.0 |
| 240 | 0.19 | 0.290 | 51.2 |
| 245 | 0.18 | 0.345 | 45.0 |
| 250 | 0.17 | 0.400 | 40.0 |
| 255 | 0.16 | 0.438 | 36.6 |
| 259 | 0.16 | 0.443 | 36.0 |
| 260 | 0.16 | 0.441 | 36.1 |
| 263 | 0.16 | 0.429 | 37.2 |
| 265 | 0.16 | 0.418 | 38.4 |
| 270 | 0.16 | 0.375 | 42.0 |
| 275 | 0.16 | 0.325 | 47.4 |
| 280 | 0.15 | 0.270 | 53.8 |
| 285 | 0.15 | 0.215 | 61.0 |
| 290 | 0.15 | 0.165 | 68.5 |
| 295 | 0.14 | 0.118 | 76.0 |

4.5 ml of 50 ppm S. flexneri were diluted to 30 ml. The final concentration is 7.5 ppm.

TABLE 6
UV ABSORPTION DATA FOR THE MIXTURE OF

E. COLI 0127:B8, 50 ppm
E. COLI 055:B5, 50 ppm
S. ABORTUS EQUI, 50 ppm      } BACTO-LIPOPOLYSACCHARIDE
S. ENTERITIDIS, 50 ppm
S. FLEXNERI, 50 ppm

| Wavelength nm | Slit Width mm | Absorbance | Transmittance Per Cent |
|---|---|---|---|
| 220 | 0.28 | 0.390 | 40.8 |
| 225 | 0.24 | 0.287 | 51.7 |
| 230 | 0.22 | 0.245 | 57.0 |
| 233 | 0.20 | 0.250 | 56.2 |
| 234 | 0.20 | 0.251 | 56.0 |
| 235 | 0.20 | 0.260 | 55.0 |
| 240 | 0.19 | 0.297 | 50.4 |
| 245 | 0.18 | 0.350 | 44.6 |
| 250 | 0.17 | 0.400 | 40.0 |
| 255 | 0.16 | 0.416 | 37.7 |
| 257 | 0.16 | 0.419 | 38.2 |
| 258 | 0.16 | 0.420 | 38.0 |
| 259 | 0.16 | 0.419 | 38.2 |
| 260 | 0.16 | 0.418 | 38.4 |
| 263 | 0.16 | 0.410 | 39.0 |
| 265 | 0.16 | 0.400 | 40.0 |
| 270 | 0.16 | 0.355 | 44.0 |
| 275 | 0.16 | 0.300 | 50.0 |
| 280 | 0.15 | 0.240 | 57.7 |
| 285 | 0.15 | 0.185 | 65.2 |
| 290 | 0.15 | 0.136 | 73.8 |

TABLE 6-continued
UV ABSORPTION DATA FOR THE MIXTURE OF

E. COLI 0127:B8, 50 ppm  
E. COLI 055:B5, 50 ppm  
S. ABORTUS EQUI, 50 ppm  } BACTO-LIPOPOLYSACCHARIDE  
S. ENTERITIDIS, 50 ppm  
S. FLEXNERI, 50 ppm

| Wavelength nm | Slit Width mm | Absorbance | Transmittance Per Cent |
|---|---|---|---|
| 295 | 0.15 | 0.088 | 81.8 |

20 ml of each solution were mixed to a final volume of 1000 ml. 4.5 ml of the 50 ppm solution of the above mixture were diluted to 30 ml. The final concentration is 7.5 ppm.

The absorption maxima for all individual endotoxins are essentially the same, i.e., 259 mm. For the five endotoxin mixtures, the absorption maxima shifted slightly toward a lower wavelength, 258 mm, and the peak broadened to some extent. From this point on, all of the absorption measurements were made at 258 mm.

In order to examine the linearity of the absorption-vs-concentration curve, a 1-liter solution of the five endotoxins cited above, containing a total of 50 ppm, was prepared by mixing 200 ml of each 50 ppm endotoxin solution in a 1-liter volumetric flask. This stock solution was kept refrigerated at 10° C. The stock solution was diluted to prepare a series of standards to be used in making the standard curve. These colutions had concentrations ranging from 10 ppb to 10 ppm. As shown in Table 7, the solutions were divided into three groups; the first having concentrations of 10–50 ppb; the second and the third having concentrations of 50–1000 and 500–10,000 ppb respectively. The absorption data for the standard solutions are shown in Table 8.

With the exception of Group 1, all other measurements were made at 258 nm and with a salt width of 0.16mm with the Beckman DU Spectrophotometer. Group 1 measurements required a more sensitive and elaborate measuring instrument. The ACTA MVI was used for the measurements.

The settings of the ACTA MVI Spectrophotometer were kept constant throughout the experiment as indicated below:

| | |
|---|---|
| Scanning Wavelength Range | : 300–225 nm |
| Scanning Speed | : 1/2 nm/sec |
| Chart Display | : 10 nm/inch |
| Chart Speed | : 1 inch/min |
| Period Set | : 0.5 |
| Span | : 0.1 |

TABLE 7
STANDARD SOLUTIONS OF ENDOTOXIN MIXTURE USED FOR PREPARING THE STANDARD CURVES

| | Concentration ppb | ppm |
|---|---|---|
| GROUP 1 | | |
| Blank-double distilled water | 0 | 0.000 |
| 0.2 ml of stock solution diluted to 1-liter | 10 | 0.010 |
| 0.5 ml of stock solution diluted to 1-liter | 25 | 0.025 |
| 1.0 ml of stock solution diluted to 1-liter | 50 | 0.050 |
| GROUP 2 | | |
| 1.0 ml of stock solution diluted to 1-liter | 50 | 0.050 |
| 2.0 ml of stock solution diluted to 1-liter | 100 | 0.100 |
| 3.0 ml of stock solution diluted to 1-liter | 150 | 0.150 |
| 4.0 ml of stock solution diluted to 1-liter | 200 | 0.200 |
| 5.0 ml of stock solution diluted to 1-liter | 250 | 0.250 |
| 7.0 ml of stock solution diluted to 1-liter | 350 | 0.350 |
| 8.0 ml of stock solution diluted to 1-liter | 400 | 0.400 |
| 10.0 ml of stock solution diluted to 1-liter | 500 | 0.500 |
| 15.0 ml of stock solution diluted to 1-liter | 750 | 0.750 |
| 20.0 ml of stock solution diluted to 1-liter | 1000 | 1.000 |
| GROUP 3 | | |
| 10.0 ml of stock solution diluted to 1-liter | 500 | 0.500 |
| 20.0 ml of stock solution diluted to 1-liter | 1000 | 1.000 |
| 30.0 ml of stock solution diluted to 1-liter | 1500 | 1.500 |
| 50.0 ml of stock solution diluted to 1-liter | 2500 | 2.500 |
| 100.0 ml of stock solution diluted to 1-liter | 5000 | 5.000 |
| 150.0 ml of stock solution diluted to 1-liter | 7500 | 7.500 |
| 200.0 ml of stock solution diluted to 1-liter | 10000 | 10.000 |

TABLE 8
UV ABSORBANCE AND TRANSMITTANCE DATA FOR SOLUTIONS OF THE ENDOTOXIN MIXTURE USED FOR PREPARING STANDARD CURVES

| Concentration ppb | Absorbance | Transmittance Per Cent |
|---|---|---|
| GROUP 1 | | |
| Double Distilled Water | 0.0019 | 99.8 |
| 10 | 0.0042 | 99.0 |
| 25 | 0.0061 | 98.5 |
| 50 | 0.0090 | 98.0 |
| GROUP 2 | | |
| 50 | 0.009 | 98.0 |
| 100 | 0.012 | 97.2 |
| 150 | 0.014 | 96.8 |
| 200 | 0.018 | 96.0 |
| 250 | 0.020 | 95.5 |
| 350 | 0.026 | 94.2 |
| 400 | 0.028 | 93.6 |
| 500 | 0.033 | 92.8 |
| 600 | 0.038 | 91.7 |
| 750 | 0.048 | 89.5 |
| 1000 | 0.062 | 86.8 |
| GROUP 3 | | |
| 500 | 0.033 | 92.8 |
| 1000 | 0.062 | 86.8 |
| 1500 | 0.091 | 81.1 |
| 2500 | 0.146 | 71.5 |
| 5000 | 0.288 | 51.5 |
| 7500 | 0.419 | 38.1 |
| 10000 | 0.575 | 26.7 |

The absorbance for each group is linear with concentration indicating that Beer's law is obeyed.

It is apparent from the data that a convenient and accurate method has been developed for monitoring the concentration of endotoxins whose identities are known. It is capable of detecting endotoxins at levels of a few ppb.

What is claimed is:

1. A method for assaying endotoxins in aqueous liquids comprising the following steps:
    a. introducing a known volume of an aqueous liquid containing lipopolysaccharide endotoxins of the bacteria selected from the group consisting of *E. coli* 0127:B8, *E. coli* 055:B5, *S. abortus equi*, *S. enteritidis* and *S. flexneri*
    b. maintaining the temperature of the sample in the cell at between 20° and 30° C,
    c. passing ultra-violet radiation of a wave length between 200 and 800 nm thru said liquid sample in the cell,
    d. measuring the absorbance of the detecting radiation at 259 nm.

2. The method according to claim 1 wherein the endotoxins are present in the solution in a connection of between 10 and 10,000 ppb.

3. The method according to claim 1 wherein, in addition to detecting radiation, reference radiation is passed through the liquid in the cell, said reference radiation being of a wavelength weakly absorbed by the liquid.

* * * * *

UNITED STATES PATENT OFFICE
CERTIFICATE OF CORRECTION

Patent No. 4,093,381   Dated June 6, 1978

Inventor(s) Narbik A. Karamian

It is certified that error appears in the above-identified patent and that said Letters Patent are hereby corrected as shown below:

Column 7, line 38, "salt" should be -- slit --.

Column 8, claim 2, line 2, "connection" should be -- concentration --.

Signed and Sealed this

Sixth Day of February 1979

[SEAL]

Attest:

RUTH C. MASON
Attesting Officer

DONALD W. BANNER
Commissioner of Patents and Trademarks